United States Patent
Sharma et al.

(10) Patent No.: US 6,309,999 B1
(45) Date of Patent: Oct. 30, 2001

(54) PROCESS FOR THE PREPARATION OF AN IMMUNOADSORBENT MATRIX

(76) Inventors: Chandra P. Sharma, 38, C.G.S. Nagar, Pappanamcode, Trivandrum-695 018; P. R. Hari, T.C. 8/1142(5), C-23(1) Mythri Nagar, Valiyavila, Thirumala, P.O. Trivandrum-695 006; Willi Paul, Prathyucha, Ollur P.O. Trichur, all of (IN)

( * ) Notice: Subject to any disclaimer, the term of this patent is extended or adjusted under 35 U.S.C. 154(b) by 0 days.

(21) Appl. No.: 09/272,304

(22) Filed: Mar. 19, 1999

(51) Int. Cl.[7] ............... B01J 20/22; B01J 20/26; C08G 63/48; C08G 63/91; C08F 8/00
(52) U.S. Cl. ............... 502/401; 502/402; 502/403; 525/57; 525/61
(58) Field of Search ............... 502/401–403; 525/57, 61

(56) References Cited

U.S. PATENT DOCUMENTS

| | | | |
|---|---|---|---|
| 3,673,612 | * | 7/1972 | Merrill et al. ............... 3/1 |
| 4,028,315 | * | 6/1977 | Bodanszky et al. ............... 260/78 A |
| 4,329,383 | * | 5/1982 | Joh ............... 428/36 |
| 4,387,183 | * | 6/1983 | Francis ............... 525/54.23 |
| 4,530,964 | * | 7/1985 | Machovich et al. ............... 525/61 |
| 5,071,973 | * | 12/1991 | Keller et al. ............... 536/8 |
| 5,574,097 | * | 11/1996 | Klaveness et al. ............... 525/61 |
| 5,760,200 | * | 6/1998 | Miller et al. ............... 536/21 |

* cited by examiner

Primary Examiner—Elizabeth D. Wood
Assistant Examiner—Patricia L. Hailey
(74) Attorney, Agent, or Firm—Venable; George H. Spencer; Ashley J. Wells

(57) ABSTRACT

A process for the preparation of an immunoadsorbent matrix includes preparing polyvinyl alcohol beads by partially crosslinking polyvinyl alcohol (PVA) with a crosslinking agent to provide polyvinyl alcohol beads which are at least partially crosslinked; coupling phenylalanine onto the polyvinyl alcohol beads to obtain a —COOH functionality for the phenylalanine coupled polyvinyl alcohol beads; and activating the —COOH functionality for immobilizing heparin onto the phenylalanine coupled polyvinyl alcohol beads.

9 Claims, 1 Drawing Sheet

US 6,309,999 B1

PROCESS FOR THE PREPARATION OF AN IMMUNOADSORBENT MATRIX

FIELD OF INVENTION

This invention relates to a process for the preparation of immunoadsorbent matrix based on modified polyvinyl alcohol microspheres and its use in columns for direct haemoperfusion.

BACKGROUND OF INVENTION

Plasma exchange has become the most common and effective therapeutic treatment of various intractable disorders and neurological diseases. Unavailability and high price of plasma products, and risk of infections lead to the development of plasma treatment devices. Selective adsorption plasma treatment is now a well established clinical practice for the treatment of myasthenia gravis, Guillain-Barre syndrome (GBS), systemic lupus erythematosus (SLE) etc., but is only marginally cheaper than plasma exchange procedure, and the columns are meant for plasma perfusion only. However, this can eliminate the dependence of plasma products on plasmapheresis thereby avoiding risk of infections. Though various immunoadsorption columns for plasma perfusion only are available, it is still not known to have direct haemoperfusion columns. Further, it is not known to have devices that can simplify and reduce treatment cost further by achieving plasma separation and plasma treatment in a single device or direct haemoperfusion.

An apparatus and method is known in the art which draws blood through a blood pump and a column, and functions as a plasma separator to cause a separation of the blood cells from the plasma. The plasma is then passed through an immunoadsorbent column so that IgG proteins get adsorbed in the adsorbent, and the treated plasma is then mixed with the removed blood cells and returned to the patient. The disadvantage of such a method and apparatus is that of substantial costs. Further, such a method is to be repeated once or twice and each time the column and plasma separator is to be replaced.

Yet another method and apparatus known in the art is to withdraw the blood of a patient, which is then centrifuged to remove the plasma, which is then replaced by fresh blood plasma from a donor. A disadvantage of such a method and apparatus is that of infection in the fresh blood of a donor. Further, hemolysis can occur in the centrifuge.

OBJECTS OF THE INVENTION

An object of this invention is to propose a process for the preparation of an immunoadsorbent matrix based on polyvinyl alcohol micropheres for direct haemo-perfusion.

A further object of this invention is to propose a process for the preparation of an immunoadsorbent matrix based on polyvinyl alcohol which can specifically remove IgG proteins from blood and is highly blood compatible.

A still further object of this invention is to propose an immunoadsorbent column based on the immunoadsorbent matrix for the specific removal of antibodies belonging to or consisting of immunoglobulins of the class G and circulating immune complexes.

Yet another object of this invention is to propose an immunoadsorbent column which can be used for direct perfusion of human patient blood for the treatment of IgG mediated disorders.

Another object of this invention is to propose an immunoadsorbent column for blood perfusion which may be applied clinically as a less complex and inexpensive alternative to plasma treatment devices.

Further objects and advantages of this invention will be more apparent from the ensuing description.

DESCRIPTION OF INVENTION

According to this invention there is provided a process for the preparation of an immunoadsorbent matrix comprising in the steps of:

a) preparing polyvinyl alcohol beads by partially cross linking polyvinyl alcohol with a cross linking agent;

b) coupling phenylalanine onto the polyvinyl alcohol beads to obtain a COOH functionality of the phenylalanine polyvinyl alcohol beads;

c) activating said COOH functionality for immobilizing heparin onto said phenylalanine coupled beads.

In accordance with this invention the preparation of immunoadsorbent beads comprises in preparing partially crosslinked polyvinyl alcohol (PVA) beads by mixing an aqueous solution of PVA with glutaraldehyde and dispersing the mixture in an oil medium by stirring. To the dispersed PVA solution is added benzoyl choloride slowly dropwise. On completion of reaction, the beads thus formed are subjected to the steps of filtering, washing, drying and sieving to obtain the crosslinked PVA beads. The dry crosslinked beads are subjected to swelling in an alkaline medium followed by filtering and then adding a mixture of epichlorohydrin and 1,4-dioxan to the swollen beads and the reaction is performed by heating. The reaction mixture is cooled and followed by washing and subjecting the washed beads to treatment with aminoacid solution with gentle stirring, and washing the beads to obtain aminoacid coupled PVA beads. The amino acid coupled beads are activated by exposing them to 1-ethyl-3-(3-dimethyl amino propyl) carbodimide in PBS (phosphate buffered saline) followed by the step of exposing the activated beads to heparin solution, washing to remove unbound heparin, to obtain the immunoadsorbent beads, Hep-ph-PVA.

The first step of the process consists in preparation of polyvinyl alcohol (PVA) beads. For this purpose, partially crosslinked PVA beads are prepared by acid catalyzed reaction missing an aqueous solution of PVA of molecular weight 100,000 to 150,000 in 3 to 6 ml of glutaraldehyde and dispersed in an oil medium and subjected to the step of stirring. Upon the PVA solution being completely dispersed, a catalyst is added dropwise. The catalyst by way of example, is benzoyl chloride. After completion of the reaction in a period of approximately 30 mins, the beads are filtered, washed, dried and classified.

The oil medium used in the cross linking of PVA beads is heavy and light liquid paraffin oil in a proportion for example 2:1, with sorbitan monooleate added thereto. Preferably, approximately 500 ml. oil solution contains about 355 ml. of heavy oil and 165 ml. of light oil with 0.4 ml. of sorbitan monooleate.

The washing of the beads is done using organic solvents preferably petroleum ether followed by acetone and subsequently with distilled water.

DESCRIPTION OF DRAWINGS

The next step in the process comprises in phenylalanine coupling onto the PVA microspheres is achieved according to the reaction scheme (Scheme I) shown in FIG. 1 of the accompanying drawing.

Stable aminoacid ligands are coupled onto the beads by swelling. Known amounts of dry beads were swollen in an alkaline medium and filtered. A mixture of epichlorohydrin and organic solvent such as 1,4-dioxan was added into the swollen beads and the reaction was performed at 100–120° C. for one hour. The mixture is cooled to room temperature, followed by through washing with acetone and distilled water to remove the excess reaction mixture and finally to neutrality. The phenylalanine is coupled to the activated beads by treating them with 250 mg % and above aminoacid solution at 40–60° C. with gentle stirring. The beads were washed free of uncoupled aminoacid. The possible reaction is depicted in FIG. 1.

The beads are washed free of the uncoupled amino acid by acetone and distilled water and finally to neutrality.

Figure 1:
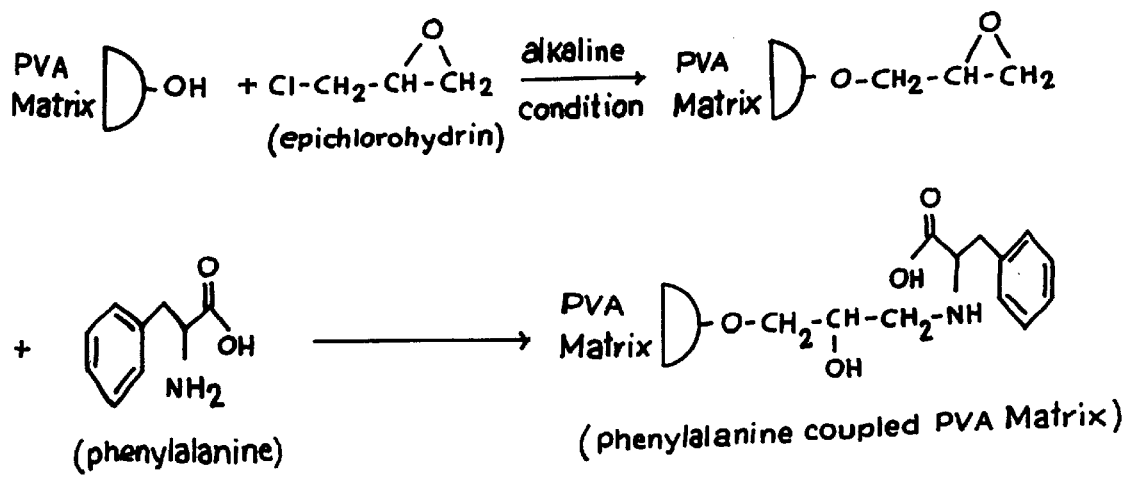
Figure 2:
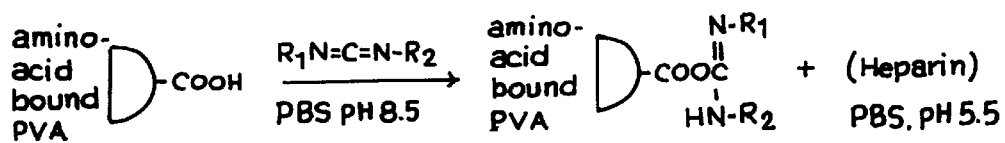
Figure 2:
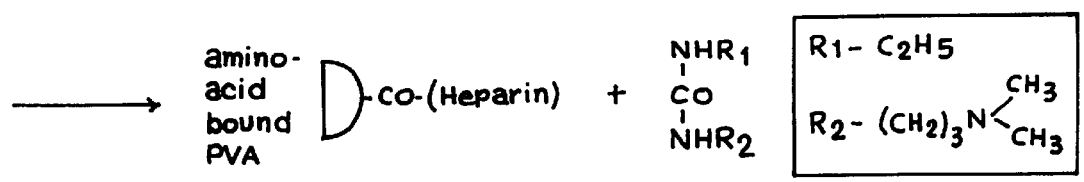

Immobilization of heparin onto the phenylalanine coupled beads is completed according to the reaction scheme (Scheme II) as shown in FIG. 2 of the accompanying drawings.

The aminoacid coupled PVA beads (wet) are exposed to 1-ethyl-3-(3-dimethyl aminopropyl) carbodimide in PBS. The activated beads are washed with distilled water followed by exposure to 4–25 mg % heparin solution in PBS to obtain adsorbents with different amount of bound heparin. The Hep-ph-PVA beads are then washed with distilled water to remove unbound heparin.

The two reactions are carried out at room temperature with gentle stirring, at a pH of about 8.5 and 5.5 respectively.

In accordance with another embodiment of the present invention, a column is packed with the Hep-ph-PVA beads and used in haemo-perfusion for the specific removal of antibodies that belong to or consist of imunoglobulins of G, i.e. antibodies such as anti-DNA, AChRab, anti-GBM and circulating immune complexes.

Other objects and advantages of the present invention will be apparent from the accompanying examples and the comparative study depicted in the following tables.

TABLE I

Platelet, RBC and WBC count before and after perfusion of calf blood (x 1000/cmm) through the columns packed with respective adsorbents.

| Cells | Control blood | CL-PVA | ph-PVA | Hep-ph-PVA |
|---|---|---|---|---|
| RBC | 4090 ± 163 | 4070 ± 139 | 4090 ± 173 | 4110 ± 169 |
| WBC | 154 ± 7.5 | 151 ± 6.3 | 150 ± 7.2 | 152 ± 7.6 |
| Platelets | 56.2 ± 2.3 | 55.8 ± 3.2 | 56.1 ± 2.3 | 55.9 ± 3.5 |

TABLE II

Reduction rate (RR %) of immunoproteins and C3 after perfusion of patient blood through the column for 1 hour.

| Matrix | Time of Perfusion | IgG | IgM | IgA | C3 |
|---|---|---|---|---|---|
| ph-PVA | 15 min. | 7.10 | 2.40 | 3.76 | 11.81 |
|  | 30 min. | 31.35 | 7.21 | 7.52 | 14.44 |
|  | 1 hr. | 41.08 | 14.42 | 9.13 | 22.23 |

TABLE III

Pre- & post-perfusion (1 hr) level of total protein and biochemical parameters.

|  | Pre-perfusion | Post-perfusion |
|---|---|---|
| Total protein | 6.02 (g %) | 5.02 (g %) |
| Urea | 6.05 (mg %) | 5.86 (mg %) |
| Creatinine | 1.22 (mg %) | 1.23 (mg %) |
| Hemolysis |  | 1.24% |

TABLE IV

Reduction Rate (%) of immunoproteins and C3 after in vitro haemoperfusion of 60 ml of human blood through a column packed with 24 grams (wet) of heparinised matrix at a flow rate of 12 ml/min.

| Matrix | Time of Perfusion | RR % | | | |
|---|---|---|---|---|---|
|  |  | IgG | IgM | IgA | C3 |
| Hep-ph-PVA | 15 min | 8.9 ± 0.9 | 2.7 ± 0.1 | 2.1 ± 0.4 | 1.8 ± 0.1 |
|  | 30 min | 16.5 ± 0.6 | 11.8 ± 2.3 | 4.7 ± 1.7 | 2.2 ± 0.6 |
|  | 1 hr | 30.1 ± 0.8 | 12.9 ± 0.8 | 6.2 ± 0.4 | 9.9 ± 1.2 |

What is claimed is:

1. A process for the preparation of an immunoadsorbent matrix, comprising:
    preparing polyvinyl alcohol beads by partially crosslinking polyvinyl alcohol (PVA) with a crosslinking agent to provide polyvinyl alcohol beads which are at least partially crosslinked;
    coupling phenylalanine onto the polyvinyl alcohol beads to obtain a —COOH functionality for the phenylalanine coupled polyvinyl alcohol beads; and
    activating the —COOH functionality of immobilizing heparin onto the phenylalanine coupled polyvinyl alcohol beads.

2. The process as claimed in claim 1, wherein preparing polyvinyl alcohol beads is accomplished by:
    mixing an aqueous solution of PVA with glutaraldehyde to provide a mixture;
    dispersing the mixture in an oil medium by stirring to provide a dispersed PVA solution;
    adding benzoyl chloride slowly dropwise to the dispersed PVA solution to form beads;
    and, on substantial completion of reaction,
    subjecting the beads formed to filtering, washing, drying and sieving to obtain the polyvinyl alcohol beads.

3. The process as claimed in claim 2, wherein the oil medium comprises heavy and light liquid paraffin oil, and sorbitan monooleate.

4. The process as claimed in claim 2, further comprising, in the order recited:
    subjecting the polyvinyl alcohol beads after drying to swelling in an alkaline medium to provide swollen beads;
    filtering;
    adding a mixture of epichlorohydrin and 1,4-dioxan to the swollen beads;
    heating at a temperature effective to cause reaction of the mixture with the swollen beads and provide a reaction mixture;
    cooling the reaction mixture;
    washing the reaction mixture to provide washed beads:

subjecting the washed beads to treatment with phenylalanine solution with gentle stirring to provide treated beads; and washing the treated beads to obtain phenylalanine coupled polyvinyl alcohol beads.

5. The process as claimed in claim 4, wherein activating the —COOH functionality is accomplished by:

exposing the phenylalanine coupled polyvinyl alcohol beads to 1ethyl-3-(3-dimethyl amino propyl) carbodimide in phosphate buffered saline (PBS) to provide activated beads;

exposing the activated beads to heparin solution; and washing the activated beads after exposing to the heparin solution to remove unbound heparin solution and obtain immunoadsorbent beads, Hep-ph-PVA.

6. The process as claimed in claim 5, wherein the heparin solution contains from 4 to 25 weight % heparin in phosphate buffered saline (PBS).

7. The process as claimed in claim 4, wherein the mixture of epichlorohydrin and 1,4-dioxan contains a ratio of epichlorohydrin to 1,4-dioxan of 1:1.

8. The process as claimed in claim 4, wherein heating at a temperature effective to cause reaction of the mixture is at a temperature ranging from 100 to 120° C.

9. The process as claimed in claim 4, wherein subjecting the washed beads to treatment with amino acid solution takes place at a temperature ranging from 40 to 60° C. for about 4 hours.

* * * * *